US006652487B1

(12) United States Patent
Cook

(10) Patent No.: US 6,652,487 B1
(45) Date of Patent: Nov. 25, 2003

(54) VENIPUNCTURE ASSISTOR

(76) Inventor: Richard S. Cook, 1440 N. Lake Shore Dr., Chicago, IL (US) 60610-1679

( * ) Notice: Subject to any disclaimer, the term of this patent is extended or adjusted under 35 U.S.C. 154(b) by 0 days.

(21) Appl. No.: 09/207,503

(22) Filed: Dec. 8, 1998

Related U.S. Application Data

(63) Continuation of application No. 08/804,937, filed on Feb. 24, 1997, now abandoned.

(51) Int. Cl.⁷ ............................................. A61M 5/00
(52) U.S. Cl. ................................. 604/115; 604/116
(58) Field of Search ........................ 604/116, 115, 604/180, 174, 179, 177, 158; 128/DIG. 26, DIG. 6

(56) References Cited

U.S. PATENT DOCUMENTS

| | | | | |
|---|---|---|---|---|
| 1,561,116 A | | 11/1925 | Silliman ................. 604/115 |
| 1,824,516 A | | 9/1931 | Tyvand .................. 128/133 |
| 2,103,174 A | | 12/1937 | Posada .................. 128/215 |
| 2,234,961 A | | 3/1941 | Canada .................. 128/327 |
| 3,324,854 A | | 6/1967 | Weese ................... 128/215 |
| 3,901,226 A | * | 8/1975 | Scardenzan ............. 128/133 |
| 4,196,735 A | * | 4/1980 | Ayer .................... 128/327 |
| 4,314,568 A | | 2/1982 | Loving .................. 128/327 |
| 4,316,461 A | | 2/1982 | Marais et al. ........... 128/214 R |
| 4,332,248 A | | 6/1982 | DeVitis ................. 128/214 R |
| 4,586,924 A | | 5/1986 | Lanning ................. 604/115 |
| 4,679,553 A | * | 7/1987 | Proulx et al. ........... 128/133 |
| 4,842,582 A | * | 6/1989 | Mahurkar ................ 604/43 |
| 5,112,313 A | * | 5/1992 | Sallee .................. 604/180 |
| 5,167,629 A | * | 12/1992 | Vertenstein et al. ..... 604/116 |
| 5,242,453 A | * | 9/1993 | Gubich .................. 604/115 |
| 5,254,095 A | | 10/1993 | Harvey .................. 604/115 |
| 5,343,875 A | * | 9/1994 | Chase ................... 128/846 |
| 5,413,562 A | * | 5/1995 | Swauger ................. 604/179 |
| 5,415,647 A | | 5/1995 | Pisarik ................. 604/115 |
| 5,449,349 A | * | 9/1995 | Sallee et al. .......... 604/180 |
| 5,693,032 A | * | 12/1997 | Bierman ................. 604/180 |

* cited by examiner

Primary Examiner—Brian L. Casler
Assistant Examiner—Cris L. Rodriguez
(74) Attorney, Agent, or Firm—James W. Clement; Michael R. McKenna

(57) ABSTRACT

A venipuncture assistor for use in inserting a needle into a patient's vein in order to draw blood or to carry out an intravenous treatment of some type. The distended vein is received in a pair of substantially rigid, spaced, opposing notches in the bottom edge of the cylindrical body of the assistor. The notches are preferably spaced about 16 mms. from each other. The space between notches is substantially free of any member that contacts the vein segment being punctured. The edges of each notch and the bottom edge of the assistor are free of any sharp protuberances. The assistor keeps the vein segment being punctured from moving laterally out of the path of the needle that is being introduced into the vein segment. It is preferably made of a transparent plastic material.

9 Claims, 1 Drawing Sheet

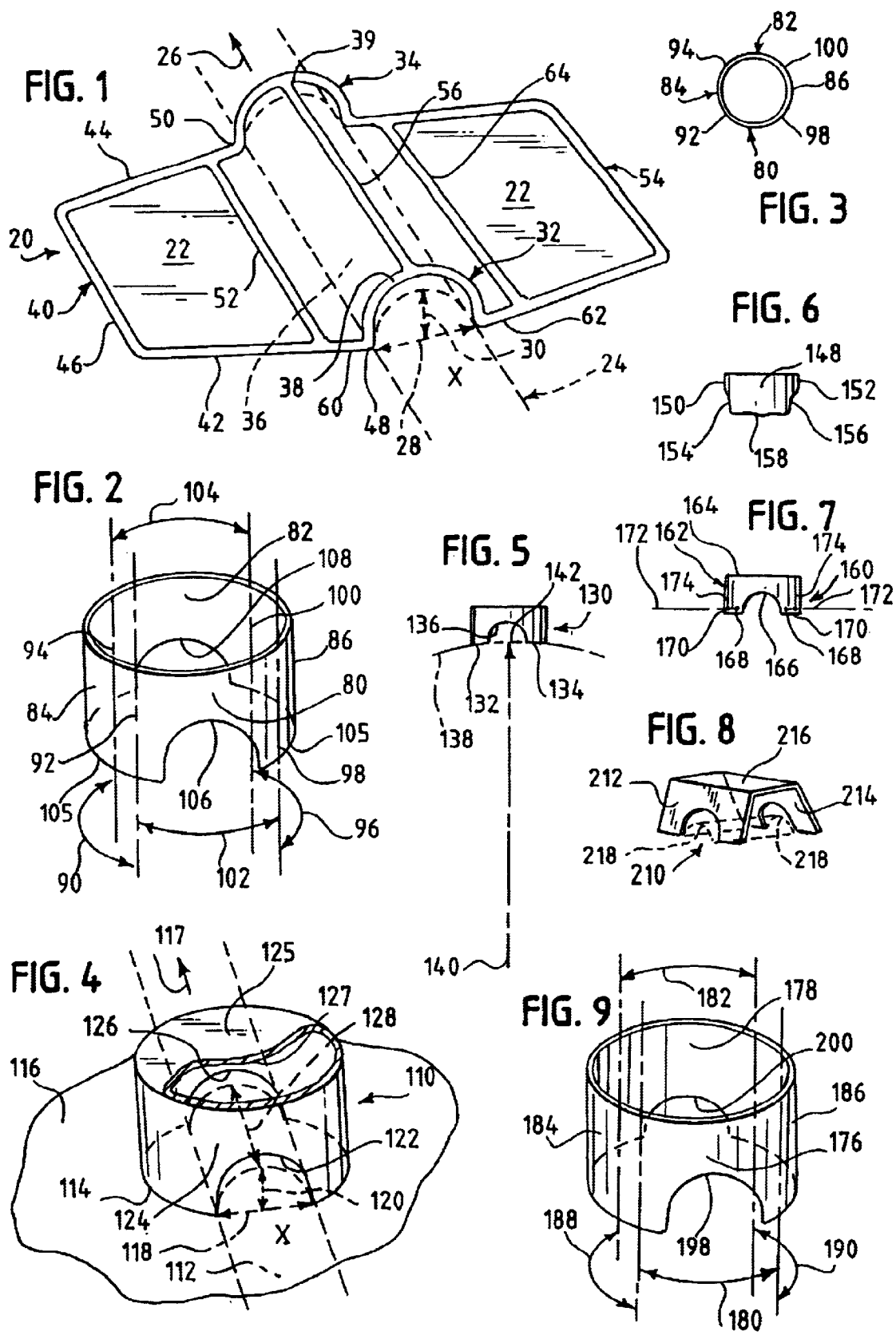

VENIPUNCTURE ASSISTOR

This application is a continuation of application Ser. No. 08/804,937, filed Feb. 24, 1997, now abandoned.

FIELD OF INVENTION

This invention relates to a device for use in venipuncture, i.e., the insertion of a needle into a patient's vein in order to draw blood, or to carry out an intravenous treatment of some type.

BACKGROUND OF INVENTION

In performing a venipuncture, the nurse, medical technician or other qualified person always seeks to accomplish the task of inserting the needle—in order to draw blood, start intravenous fluids, or inject some medication—on the first trial. If the first attempt is not successful and another attempt must be made, the patient's discomfort and anxiety are increased, the chances of infection are increased, and the number of sites available for future venipuncture is further decreased. Hence it is important to make the likelihood of a successful insertion on the first try as great as possible.

In the insertion of a needle into a vein, the needle is positioned directly over the chosen vein at an angle that is selected (1) to avoid pushing the needle completely through the vein and out the opposite side, and (2) to bring the tip of the needle into an appropriate final position so that blood can flow back into the hollow needle, or fluids can flow through the needle into the vein. The vein is surrounded and supported by fatty tissue in the cells that make up the connective tissue, and it lies between the skin and the underlying muscle or bone.

Most persons performing a venipuncture sense the depth of the vein below the skin surface by touch as well as by sight. Another source of information for the person doing the venipuncture is the "feel" of the needle tip as it is inserted in the patient's arm or other body part. The needle is first pressed through the skin, which is felt as one layer, then through the intervening fatty tissue as a second layer, and finally through the wall of the vein, which is felt as a third layer. The angle at which the needle is inserted may be adjusted as the venipuncture proceeds, and will usually be changed at least in the latter part of the procedure so that the tip of the needle will stay within the vein.

During this procedure any extreme lateral movement of the vein as the needle is being inserted must be avoided. However, the vein is often difficult to hold steady, as it tends to roll, or move sideways, entirely out of the path followed by the needle as the needle is pressed into the tissue above the vein. When this happens, the tip of the needle pushes the vein aside, the venipuncture is unsuccessful, and another attempt to insert the needle in the patient's vein must be made.

Sometimes the person inserting the needle will try to use his or her fingers to prevent the vein from rolling out of the path of the needle being inserted. This poses the risk of puncturing a finger with the needle, thereby increasing the chance of the operator getting a blood borne disease such as hepatitis B or HIV.

Various complicated, bulky, or cumbersome instruments have been developed for keeping a vein from moving laterally out of the way of the needle as it is being inserted during venipuncture.

U.S. Pat. No. 1,561,116, issued to Silliman on Nov. 10, 1925, discloses a vein stabilizer that has a flat metal plate (or a similar shape formed of wire) for pressing down upon a portion of a distended vein while an immediately adjacent portion of the vein is contained in an opening that is directed towards the heart.

U.S. Pat. No. 1,824,516, issued to Tyvand on Sep. 22, 1931, discloses a vein retainer comprising a complicated plate structure (which carries a pair of adjustable retaining fingers having downwardly turned ends) that is placed over a vein and held there tightly by an adjustable strap. The two fingers carried by the plate press down against the body surface on both sides of a vein for the entire length of the involved portion of the vein, and a third finger (which, extends downwardly from the plate and is positioned transverse to the path of blood flow) pushes down against the vein and restricts the flow of blood so as to distend the vein.

U.S. Pat. No. 2,103,174, issued to Posada on Dec. 21, 1937, discloses a surgical instrument having a plate that comprises a pair of upwardly bowed legs that are connected by spring means to form an opening between the legs, the spring means being manipulable by pressing down separately with the operator's thumb and index finger applied to the bowed legs in order to narrow the width of the opening that retains the vein, and to confine the vein segment being punctured to cause it to swell up and stand out in bold relief.

U.S. Pat. No. 2,234,961, issued to Canada on Mar. 18, 1941, discloses a mechanism consisting of a tourniquet to which a pivoted metal device is attached. This device has two downsloping legs that can be positioned to press downward at a single narrow location on either side of the vein to be punctured.

U.S. Pat. No. 3,324,854, issued to Weese on Jun. 13, 1967, discloses a vein-stabilizing device that is adapted to be attached to the barrel of a syringe and which includes two leg portions (joined by a connecting member) that initially extend beyond the point of the needle and can be pressed down on both sides of the portion of the vein to be punctured, which causes the connecting member to press down against the vein as well, at a location only a short distance beyond the point at which the needle enters the flesh above the vein.

U.S. Pat. No. 4,314,568, issued to Loving on Feb. 9, 1982, discloses two flat members adjustably hinged (at one end only) to form an opening of variable width between them, with means to lock the members in position to press down on both sides of the vein during venipuncture.

U.S. Pat. No. 4,316,461, issued to Marais et al. on Feb. 23, 1982, discloses a long, flat, rigid rectangular base plate with a medially located opening extending for a part of the length of the plate, and a hood adapted to cover and contact the vein for a part of the length of the opening and exert downward pressure on the vein when the base plate is pressed from above. Once the intravenous needle is introduced. into the vein, the whole assembly is held in place with a pair of straps.

U.S. Pat. No. 4,332,248, issued to DeVitis on Jun. 1, 1982, discloses a device having a parallel pair of downwardly extending leg members for receiving and pressing down around a distended vein, and a third member rigidly positioned with respect to the leg members and adapted to guide a needle at a fixed angle to the vein.

U.S. Pat. No. 4,586,924, issued to Lanning on May 6, 1986, discloses a long, flat plate with a notch at one end which leads to a groove under the plate. When the device is in use, the walls of the groove press down on the vein close to the point of insertion of the needle.

U.S. Pat. No. 5,254,095, issued to Harvey on Oct. 19, 1993, discloses a stabilizer for blood vessels that looks like a shortened, widened forceps and functions similarly. It is formed of two resiliently hinged panels. with their outer edges spaced from each other. Each of the panels has a pair of downwardly extending, narrow legs that taper to thin pointed ends (disclosed as being about the thickness of a slightly dull pencil point) for engaging, and pushing inwardly when the device is manually manipulated, against the skin surrounding the vein for the positioning and stabilizing of the vein into which a needle is to be inserted.

U.S. Pat. No. 5,415,647, issued to Pisarik on May 16, 1995, discloses a vascular immobilizer consisting of a flexible, flat, elongated piece of a clear plastic or plastic-like material with a plurality of grooves on its bottom surface arranged parallel to each other and perpendicular to the longitudinal axis of the device, the grooves being of various calibers and having walls arranged at various angles to squeeze and immobilize a substantial length of the vein in the area into which the needle is to be inserted.

None of these many prior patents which are addressed to problems inherent in a venipuncture procedure discloses or suggests the venipuncture assistor of the present invention.

SUMMARY OF THE INVENTION

The venipuncture assistor of this invention is employed to keep a selected segment of a patient's vein from moving laterally out of the path of a needle that is being inserted in the selected vein segment after the flow of blood in the vein has been restricted by application of a tourniquet or similar device at a location spaced from the intended point of insertion of the needle.

In its broadest form, the device of this invention includes (1) a first substantially rigid arch configured and dimensioned to receive one of the end portions of the distended selected vein segment and associated skin and tissue in which a needle is to be inserted, and (2) a second, similarly configured and dimensioned, substantially rigid arch spaced from and facing the first arch. The arches should be parallel to each other in the horizontal plane, but need not be parallel in the vertical plane. The arches are preferably spaced from each other by a distance approximately equal to the length of vein segment that is customarily steadied, by a person skilled in venipuncture, to receive a needle during venipuncture.

As used in this specification and the accompanying claims, the term "arch" includes structures that have an overall semi-circular shape, an inverted "U" shape, an inverted "V" shape or any other suitable shape. Because each arch is substantially rigid, it will be understood that the space spanned by each of said first and second arches is substantially constant in size under any pressure that is exerted on the arches during normal use of the assistor.

At least one support member which has a downwardly facing bottom surface fixedly and substantially rigidly interconnects the two arches. Each of the arches has (1) a lower portion on each side thereof, each of which lower portions has a bottom edge and a generally vertical inner edge that faces inward into the space spanned by the arch, and (2) an upper-portion which has a downwardly facing bottom edge.

The bottom edges and inwardly facing, generally vertical edges of the base portions of the arches and the bottom surface of the at least one support member are free of any exposed sharp-protuberances. It will be understood that the term "exposed," when used in this specification or the appended claims to modify "sharp protuberances," refers to such protuberances that are located in positions to press against either the distended selected vein segment and its associated skin and tissue, or against the surrounding surface of the patient's body part in which the needle is being inserted. Several suitable shapes of the at least one support member are disclosed herein.

The space between the two arches must be substantially free of any member that presses—when the vein segment and its associated skin and tissue have become distended, because of the restriction of the flow of blood, to a given width, and to a given height above the surrounding surface of the body part in which said needle is being inserted and the assistor is in operative position over the vein that is to be punctured—against any part of the distended vein segment and associated skin and tissue. In other words, the space between the two arches constitutes a vein-accommodating space.

The invention is first disclosed in this specification, and defined in the accompanying claims, in its broadest form. In this form there is no reference to the fit between the arches and the selected vein segment and its associated skin and tissue after they have become distended, because of the restriction of the flow of blood, to a given width and to a given height. (When used in this specification and the accompanying claims, the term "associated skin and tissue" means the skin and tissue immediately above and immediately adjacent the selected vein segment. As used herein, the "given width" is measured at the level of the surrounding surface of the body part in which the needle is being inserted, and the "given height" is the height above that same surface.)

The invention is also disclosed and claimed with respect to the given width and given height just mentioned. As thus disclosed and defined, each of the two arches is configured and dimensioned to receive the end portion of the distended selected vein segment and associated skin and tissue that is adjacent the arch with an operative fit measured in the horizontal direction.

In an "operative fit" for the purposes of venipuncture, the distended vein segment and associated skin and tissue are neither too loosely nor too tightly confined in the horizontal direction by the arches of the assistor. If the horizontal fit with the arches is too loose the vein segment may not be prevented from moving out of the path of the needle, and if it is too tight there will not be enough room to insert the needle without running the risk of damaging the vein.

Good results are obtained if the fit, measured in the horizontal direction, is between a moderately loose fit and a slightly compressive fit. It is preferred that the width of the arch at its bottom be approximately equal to the given width of the distended vein segment and associated skin and tissue, thereby producing what is referred to herein as a close fit.

(The term "moderately loose fit" is used in this specification and in the accompanying claims to mean a fit that leaves space on each side no greater than approximately 20 percent of the given width of the distended vein segment and associated skin and tissue. The term "slightly compressive fit" as used herein means a fit that will reduce the horizontal dimension of the vein segment and associated skin and tissue from their given distended width by no more than about 20 percent.)

The downwardly facing bottom edge of the upper portion of each arch is at least as high as the given height of the distended vein segment and associated skin and tissue, and preferably somewhat higher. As will be seen, the result is that the edge in question does not press against the distended selected vein segment and its associated skin and tissue.

The arches are preferably spaced from each other by a distance approximately equal to the length of vein segment that is customarily steadied, by a person skilled in venipuncture, to receive a needle during venipuncture.

As mentioned above, at least one support member fixedly and substantially rigidly interconnects the two arches. If there are two such support members, one can suitably be positioned on each side of the assistor. Each support member may include two laterally extending members, with a crosspiece fixedly attached thereto and spaced from the inside edge of the base of each of the arches. The assistor may include a brace extending from the top portion of one of the arches to the top portion of the other arch.

If desired, various arrangements of panels, preferably formed of a transparent material such as plastic, may be employed as the at least one support member fixedly and substantially rigidly interconnecting the two arches.

Preferred embodiments of the venipuncture assistor of this invention include a pair of substantially rigid, spaced, opposing end walls and a pair of substantially rigid, spaced, opposing side walls fixedly and substantially rigidly connecting the respective side edges of the end walls. All of these walls are formed in major part—and preferably entirely—of a transparent material such as plastic. The walls may be planar or curved, as desired. The opposing end walls are preferably spaced from each other at their lateral midsections a distance approximately equal to the length of vein segment that is customarily steadied, by a person skilled in venipuncture, to receive a needle during venipuncture.

In these embodiments, the bottom edge of the lateral midsection of each end wall contains a notch that is configured and dimensioned to receive, with an operative fit measured in the horizontal direction, the distended vein and associated skin and tissue into which a needle is to be inserted. Good results are obtained if the fit, measured in the horizontal direction, is. between a moderately loose fit and a slightly compressive fit. It is preferred that the fit be a close fit, with the width of the notch being approximately equal to the given width of the distended vein segment and associated skin and tissue.

The portions of the end walls that define these notches correspond to the arches in the broadest form of this device that is discussed above. As used in this specification and the accompanying claims, the term "notch" includes (1) openings having an overall semi-circular shape, (2) openings portions of which are curved and portions. of which are are straight such as openings having the shape of an inverted "U," (3) openings having the shape of an inverted "V" and (4) openings having any other suitable shape.

Each of the notches is at least as high as the given height of the distended vein and associated skin and tissue, and preferably somewhat higher. As a result, the downwardly facing edge of the upper portion of the notch does not press upon the distended selected vein segment and its associated skin and tissue.

To take advantage of the economy of size provided by this invention, the end walls may suitably be spaced from each other at their lateral midsections by a distance of about 10 mm. to about 30 mm., and the side walls may be similarly spaced from each other by about 10 mm. to about 40 mm. Improved and preferred spacings are discussed below.

The major portion of the bottom edges of the end walls and side walls of these embodiments, taken together, constitutes the lowermost part of the assistor, which is located either (1). in a substantially horizontal plane or (2) in a substantially horizontally disposed portion of a cylindrical surface (a) that has a circular cross section, measured transverse to the involved vein segment, and (b) whose central axis is parallel to, and is positioned a substantial distance below, a straight line that passes through the center of the bottom boundary of each of the notches in the end walls or (3) in a generally planar surface that has a wavy cross section.

The bottom edge of each end wall and side wall of these embodiments may, if desired, be grainy, or vertically wavy, or any other appropriate shape or texture that does not cause the patient discomfort when the venipuncture assistor is pressed downward against the surface of the body part into which the needle is to be inserted. In any case, the bottom edges are free of any exposed sharp protuberances.

It is preferred that, except for the notch in each end wall, the bottom edges of the end walls and side walls in these embodiments extend substantially continuously around the perimeter of the space enclosed by the walls, and in every case these edges extend at least around the major part of that perimeter. In a particularly preferred embodiment, the end walls and side walls form a cylindrical surface and are capped with a substantially flat circular top wall. Other suitable shapes may be used.

For ease of handling and to hold the device in place above the vein in which the needle is to be inserted, the bottom portions of the side walls may be attached to strips of material, preferably adhesive tape, extending laterally on both sides of the device. In a preferred form, the bottom portions of the end walls and side walls of the inverted chamber extend approximately ½ mm. to about 1½ mm. below the strips that extend outwardly on both sides of the device.

All forms of the assistor of this invention are preferably made entirely of plastic, in order to make the vein being punctured completely visible as the needle is inserted in the vein.

ADVANTAGES OF THE INVENTION

The venipuncture assistor of this invention is small and uncomplicated in structure, which makes it easy to manufacture and easy to handle and use. It will greatly aid medical personnel in successfully drawing blood from a patient for sending to a laboratory, or inserting a needle into a patient's vein for the purpose of some intravenous treatment. Because of its structure, it can be immediately and effectively used by a nurse, a medical technician or any other qualified person, without any special training in use of the device being necessary.

The device of this invention is especially useful for inserting a needle into the smaller veins on the arm, a vein that curves near the round part of the wrist, or a smaller vein on the back of the hand. It will also be very useful when a patient's larger veins have been repeatedly pierced over a long period of time, and smaller veins must be selected for venipuncture. It will enable the person inserting the needle, even one of lesser skill, to perform venipuncture better on a difficult patient such as an elderly person, someone who is emaciated or obese, a patient in shock, or perhaps a child.

Because with this assistor the constriction of the vein to distend the same and the steadying of a vein segment are accomplished separately, it is not necessary to squeeze or bunch the patient's flesh. Use of the device produces no discomfort or pain on the patient's part, both because of the absence of pinching or bunching just mentioned and because of the absence of legs or prongs or sharp protuberances that poke into the patient's flesh.

Because of the round shape of the bottom edge of the inverted cylindrical chamber in a preferred embodiment of the device, the assistor of this invention is to an extent similar to the shape of the surface of the surrounding body part. This increases the effectiveness of the device in holding the surfaces on both sides of the vein segment taut, so that the notches at both ends of the device can better stabilize the vein as the needle is inserted.

One of the most important advantages of this invention is that the assistor can be held in place by downward pressure from one or more of the five fingers of one of the two hands of the person performing the venipuncture, and at the same time another of the five fingers of that hand can be extended to contact a side surface, or the bottom surface, of the body part in which the vein being punctured is located. This means that the latter finger can be braced against the body part to help stabilize the assistor and help the operator maintain his or her balance with respect to the patient.

Whatever the basic shape of the device may be, the short distance between the spaced arches or the notched end walls (in whatever terms the device is described) means that an a suitable length of the vein can be isolated and steadied even if the involved vein portion in its unrestrained condition is somewhat curved in its horizontal outline.

The present invention recognizes the fact that it is not necessary in venipuncture to immobilize the distended vein segment completely. It is sufficient if the vein segment into which a needle is being inserted is kept from rolling sidewise so far and so quickly that it becomes difficult to make the insertion. Sidewise movements up to approximately 1 mm. in either direction (somewhat less with smaller veins) can ordinarily be dealt with successfully by the person performing the venipuncture. It is only necessary that the vein segment to be punctured be kept by the assistor within-a practicable range for insertion of the needle.

This degree of horizontal confinement may be accomplished in all forms of the device of the present invention by providing an operative fit between the two notches or arches of the device and the distended vein segment and associated skin and tissue that are to be punctured.

In the preferred embodiments of the device, the desired degree of horizontal confinement is additionally accomplished by restraining the distended vein segment and associated skin and tissue at only two locations. These locations are strictly limited to the areas within the confines of each arch or notch described above, and exclude the entire space between opposing arches or notches.

Two facts make it possible in these preferred embodiments of the invention to achieve the desired degree of horizontal containment of the vein segment through restraints applied only at the indicated two locations. First, restriction of the flow of blood in the vein to be punctured, by application of a tourniquet or similar device at a location spaced from the intended point of insertion of the needle, produces a distended vein segment and associated skin and tissue that are significantly less flexible than when the vein is in its normal condition. Second, this increased rigidity is especially noticeable when the vein segment being restricted is as short as the selected vein segment customarily is in venipuncture.

In addition to these two facts, in those preferred embodiments of the invention that include geometric shapes whose bottom edges are pressed downward against the body surface outward of the vein segment and associated skin and tissue that are being punctured, the resulting contact tends to cause the patient's skin on either side of the vein segment to remain relatively taut, which in turn helps to hold the vein segment steady.

BRIEF DESCRIPTION OF DRAWING

FIG. 1 is an enlarged perspective view of one embodiment of the venipuncture assistor of this invention, in operative position over a distended vein segment (which is shown diagrammatically) that is to be punctured by a needle;

FIG. 2 is an enlarged perspective view of the end walls and side walls of a preferred embodiment of the device of this invention;

FIG. 3 is a plan view of. the venipuncture assistor walls of FIG. 2, showing the actual transverse dimensions of the device;

FIG. 4 is a showing of the walls of FIG. 2 with a portion of the top wall included, to illustrate a preferred form of the venipuncture assistor of this invention in place over a distended vein segment (shown diagrammatically) that is to be punctured by a needle;

FIG. 5 is an end view of another embodiment of the device of this invention;

FIG. 6 is a side view of another embodiment of the device of this invention;

FIG. 7 is an end view of the embodiment of FIG. 4 with a strip of adhesive material extending laterally on both sides of the device; and FIG. 8 is a perspective view of still other embodiment of the device of this invention in place over a distended vein segment (shown diagrammatically) that is to be punctured by a needle; and FIG. 9 is a perspective view similar to FIG. 2, showing an assistor according to this invention in which one of the notches in the bottom edge of the assistor in which has a greater height than the other.

BASIC CONCEPTS

The basic concepts utilized in the venipuncture assistor of this invention are illustrated in the embodiment of the device shown in FIG. 1. Venipuncture assistor 20 (enlarged in the original drawing as filed to approximately four times actual size) is shown positioned on surface 22 of the body part into which the needle is to be inserted. Vein 24, which is to be punctured by the needle, is shown diagrammatically.

The direction of flow of blood is indicated by arrow 26. A tourniquet or similar device (not shown in FIG. 1) for restriction of the flow of blood in the vein is located at a point beyond the arrow. The resulting restriction of blood flow has caused the vein and associated in and tissue to become distended and as a result the normal width of the vein and its associated skin and tissue, as well as the normal height of the same above body surface 22 have been increased to a given width 28 and a given height 30 respectively.

First substantially rigid arch 32 is located on the near side of the venipuncture assistor shown in FIG. 1. Second substantially rigid arch 34 is shown on the far side of FIG. 1, spaced from and facing the first arch. Segment 36 of the distended vein (lying within its associated skin and tissue) is the portion of the vein into which the needle is to be introduced after first being inserted in the vein at the general location indicated by the letter "X."

Arch 32 is configured and dimensioned to receive a distended vein segment and associated skin and tissue with an operative fit, measured in the horizontal direction. Such a fit may be, for example, between a moderately loose fit and a slightly compressive fit (as defined above in the Summary of the Invention), depending on the size of the vein. Arch 34, at the far side of the illustrated device, is similarly configured and dimensioned. With the size vein illustrated in FIG. 1, the particular fit with each arch may be considered a close fit.

The bottom edges of upper portions 38 and 39 of arches 32 and 34, respectively, are at least as high as the given height 30 of distended vein segment 24 and associated skin and tissue, and preferably somewhat higher. The bottom edges of upper portions 38 and 39 are free of any exposed sharp protuberances.

During use of this embodiment of the venipuncture assistor, arch 32 is closer to the person operating the device than arch 34. If desired, the height of arch 32 on the near side in FIG. 1 may be greater than the height of arch 34 on the far side, which will provide the operator more space in which is to make a proper puncture in the vein.

At least one support member 40 is fixedly and substantially rigidly connected to, and extends laterally from, arches 32 and 34. In the embodiment shown, support member 40 includes laterally extending members 42 and 44, which are connected at their outer ends by cross member 46.

Laterally extending members 42 and 44 are fixedly connected to base 48 of arch 32 and base 50 of arch 34, respectively.

Members 42 and 44 are also connected near their inner ends by cross brace 52, which is fixedly attached to the laterally extending members. In the device of FIG. 1, brace 52 is spaced outwardly from the inside edges of bases 48 and 50 of arches 32 and 34, respectively.

Members 42 and 44 may be curved slightly in the vertical direction to approximate the curvature of the surface of the body part on which the assistor is positioned during venipuncture.

The bottom edges of members 40, 42, 44 and 52 are all free of any exposed sharp protuberances.

It is preferred that similar support member 54 extend laterally on the right hand side of the device illustrated in FIG. 1.

In the embodiment shown in FIG. 1, brace 56 extends from top portion 38 of arch 32 to top portion 39 of arch 34.

In any case, the construction of support member 40, support member 54 (when present) and top brace 56 (when present) should be such as to provide a structure against which the operator of the device can press with his finger or fingers in order to hold the assistor in position over the vein that is to be punctured.

Arches 32 and 34 are spaced from each other a distance approximately equal to the length of vein segment that is customarily steadied, by a person skilled in venipuncture, to receive a needle during venipuncture. The spacing between arches 32 and 34 can suitably be as small as 10 mm. or as large as 30 mm. and sometimes higher, with approximately 16 mm. being preferred.

The space between the two arches be substantially free of any member that presses to any extent, when the assistor is in place over the vein that is to be punctured, against any portion of distended vein segment 36 and associated skin and tissue.

As a result of the construction described, the venipuncture assistor of this invention can be positioned to receive distended vein segment 36 and its associated skin and tissue within arches 32 and 34, and the device can be pressed downward against surface 22 of the patient's body outward of the vein segment and its associated skin and tissue. This will prevent the distended vein segment from moving out of the path of the needle as the needle is inserted by the person performing the venipuncture.

As will be understood by one skilled in the art, the various members that comprise the device of this invention can be formed of any suitable material that is sufficiently rigid to maintain the described shapes under normal pressures exerted by the user of the device to preform the necessary functions of the device.

If desired, the member forming arch 32, as well as members 60 and 62 at the base of the arch on either side thereof, can be expanded upwardly in cross section so that together they form a vertical sheet of material having a notch at the bottom edge of the sheet. Arch 34 can be similarly modified. The members forming cross braces 52 and 64 can be similarly modified to produce vertical sheets of material that connect the modified near and distant ends of the device.

The described vertical sheets of material can be configured to function as the end walls and side walls of a structure having a horizontally disposed top wall. This modified device will be similar to the preferred embodiments of the venipuncture assistor of this invention, which are described below.

Any other suitable construction that includes a pair of spaced, opposing arches and at least one support member fixedly and substantially rigidly interconnecting the arches may be utilized. FIG. 8 provides an example of the venipuncture assistor of this invention in its basic form. Venipuncture assistor 210 shown in FIG. 8 includes spaced, opposing arches 212 and 214. The arches are fixedly interconnected by support member 215, comprised of a single panel. In this embodiment the arches include the entire area of each tilted panel, and together with horizontal panel 216 have a cross section (parallel to the longitudinal axis of the vein segment being punctured) in the general shape of an inverted "U." In this embodiment, there is nothing between arches 210 and 214 that presses in any way against vein segment 218 and its associated skin and tissue. The bottom edges of the arches are free of any sharp protuberances. As will be seen, the arches are parallel to each other in the horizontal plane, but not in the vertical plane.

The panels referred to in the preceding paragraph are show in FIG. 8 as planar panels, but they may be nonplanar if desired, so long as they do not press against the distended vein segment and associated skin and tissue that are being punctured.

PREFERRED EMBODIMENTS OF INVENTION

FIGS. 2 through 7 illustrate preferred embodiments of the device of this invention.

General Construction

FIGS. 2–4 show the general construction of one example of a preferred embodiment of the venipuncture assistor of this invention.

FIG. 2 is a perspective view of substantially is rigid, spaced opposing end walls 80 and 82, and substantially rigid, spaced opposing side walls 84 and 86, all enlarged in the original drawing as filed to approximately three times the actual size of the device. End wall 80 is closer to the operator when the assistor is in use. At least major portions of the pair of end walls and pair of side walls are formed of a transparent material such as plastic, and it is preferred that they be entirely formed of such material. (The top wall of the assistor, which is seen in FIG. 4, is omitted for clarity in FIG. 2.)

As indicated by double arrow 90 in FIG. 2, side wall 84 fixedly and substantially rigidly connects side edge 92 of notch-defining end wall 80 to side edge 94—with which edge 92 is aligned—on opposing end wall 82. Similarly, as indicated by double arrow 96, side wall 86 connects side edge 98 of notch-defining end wall 80 with side edge 100 of opposing notch-defining end wall 82. Double arrows 102 and 104 also indicate the connections just described between the pair of end walls 80, 82 and side walls 84, 86. Side walls 84 and 86 function together as the support member that fixedly and substantially rigidly connects spaced, opposing, notch-defining end walls 80 and 82.

Bottom edges 105 of end walls 80, 82 and side walls 84, 86 form a smoothly curved line that is continuous except for the areas occupied by notches 106 and 108. The distances between the lateral midsections of spaced end walls 80 and 82, and of spaced side walls 84 and 86, respectively, are equal. The end walls and side walls are curved to form a cylindrical surface having its longitudinal axis disposed vertically.

FIG. 3 provides a top plan view of the structure of FIG. 2, showing the same interconnections between the end walls and the side walls of this embodiment of the device of this invention as are shown in FIG. 2. FIG. 3 is drawn in the original drawing as filed to show the actual small size of this embodiment of the venipuncture assistor of this invention, which is one of its important advantages.

As will be seen in FIG. 2, the bottom edges of the end walls and side walls are free of any sharp protuberances.

The lateral midsection of end wall 80 defines notch 106 in its bottom edge. Similarly, the lateral midsection of opposing end wall 82 defines notch 108 in its bottom edge. Each of these notches is configured and dimensioned to receive, with an operative fit, a distended vein segment and associated skin and tissue in which a needle is to be inserted. (See Summary of the Invention, above.)

FIG. 4 shows one embodiment of the venipuncture assistor of this invention in place over a distended vein segment and the associated skin and tissue (illustrated diagrammatically). Bottom edge 114 of the assistor is laterally positioned firmly against surface 116 of the patient's body outward of the vein segment and associated skin and tissue.

The direction of flow of blood is indicated by arrow 117. A tourniquet or similar device (not shown in FIG. 4) for restriction of the flow of blood in the vein is located at a point beyond the arrow. The distended vein segment and associated skin and tissue have a width 118, and a height 120 above surrounding surface 116.

Notch 122 (corresponding to notch 106 in FIG. 2) is defined by near end wall 124 of the assistor. A portion of the assistor top wall 125 is omitted in FIG. 4 to expose notch 126, which is defined by far end wall 127 of the assistor.

Notch Size and Spacing

In the embodiment shown in FIG. 4, each of notches 122 and 126 is configured and dimensioned to receive distended vein segment 128 and associated skin and tissue with a close fit measured in the horizontal direction. With smaller or larger veins than the vein illustrated in this Figure, the fit with this particular size notch may be any of several operative fits, as for example somewhere between a moderately loose fit and a slightly compressive fit (all as defined above in the Summary of the Invention).

Notches 122 and 126 are each at least as high as the height 120 of the distended vein segment and associated skin and tissue in which a needle is to be inserted. Each notch is preferably somewhat higher, in order, among other things, to provide space to receive the top portion of the distended vein segment and its associated skin and tissue if it expands vertically when the lower portion is received in the notch with a slightly compressive fit. When the fit in the notches is a slightly compressive horizontal fit, the height of each notch is greater than the given height of the distended vein segment and associated skin and tissue by at least an amount generally proportional to the percentage reduction in the given width that is caused by the slightly compressive fit. A notch height of about 25 percent above the given height of the distended vein segment and associated skin and tissue will ordinarily be adequate for this purpose.

Typically, the height and shape of the notches or arches (for example, as in FIGS. 1, 4, and 8 are such as to provide sufficient room for any upward movement of the distended vein segment and associated skin and tissue that may occur during use of the assistor. When the fit is a slightly compressive horizontal fit, the internal height of each notch or arch is preferably greater than the given height of the distended vein segment and associated skin and tissue by at least an amount generally proportional to the percentage reduction in the given width of the distended vein segment and associated skin and tissue that is caused by the slightly compressive fit.

If desired, the height of notch 122 on the near side in FIG. 4 may be greater than the height of notch 126 on the far side, which will provide the operator more space in which to make a proper puncture in the vein. This will in addition permit at least the initial portion of the vein segment to move vertically to accommodate a vertically slanted needle and thereby avoid the need scraping or puncturing the interior wall of the vein segment.

FIG. 9 illustrates how the venipuncture assistor of FIG. 4 can be modified to have notches of different heights. The cylindrical body of the assistor is formed by opposing end walls 176 and 178 (indicated by double arrows 180 and 182) and opposing side walls 184 and 186 (indicated by double arrows 188 and 190). Together the walls form the cylindrical body that has notches 198 and 200 on its bottom edge. Notch 198, which is closer to the operator when the assistor is in use, is of greater height than is notch 200 in the opposing end wall.

In addition to avoiding downward pressure from the top edge of either of the notches 122 and 126 on the distended vein segment and associated skin and tissue when the assistor is in place over the vein that is to be punctured, the space between the end walls provides a vein-accommodating space that is substantially free of any member configured and dimensioned to press in any direction against the distended vein segment and associated skin tissue.

The length 128 of the vein segment that is directly affected by use of the assistor of this invention is determined by the spacing between notches 122 and 126, which are defined by the near and far end walls of the device. The spacing between these walls is suitably approximately equal to the length of vein segment that is customarily steadied, by a person skilled in venipuncture, to receive a needle during venipuncture.

The end walls may suitably be spaced from each other at their lateral midsections by a distance of about 10 mm. to about 30 mm., and the side walls may be similarly spaced from each other by about 10 mm. to about 40 mm. In an improved form of the device, the distance between the end walls is about 10 mm. to about 20 mm., and the distance between the side walls is about 10 mm. to about 25 mm. In a still further improved form, the distances in question may be about 10 mm. to about 16 mm., and about 10 mm. to about 20 mm. In the preferred form, the distance between the end walls, as well as the distance between the side walls, is about 16 mm.

The venipuncture assistors of this invention (of whatever type) can be supplied commercially, in groups or sets of 3 or 4, with notches (or arches) of various sizes in the members of the group or set. It is believed that the notches (or arches) in such a set of venipuncture assistors can be dimensioned so that the group or set of devices can be used satisfactorily for vein segments and associated skin and tissue covering a range from about 3 mm. to about 9 mm. for the horizontal width of the distended vein segment itself (without associated skin and tissue) in which venipuncture is to be performed. If desired, a larger number of assistors of various sizes can be included in such a group or set.

Alternative Shapes

As will be seen, in the particular embodiment illustrated in FIG. 2 the distances between the lateral midsections of spaced end walls 80 and 82 and of spaced side walls 84 and 86, respectively, are equal. The bottom edges of the end walls and side walls are smoothly curved and substantially continuous except for the areas occupied by the vein-receiving notches. Together, the end walls and side walls form a cylinder having a circular horizontal cross section. With substantially flat circular top wall 125 (seen in FIG. 4), an inverted cylinder with a closed top is formed.

So long as the described notches are present, the side walls, end walls and top wall of the device of this invention may form an inverted hemisphere, an ellipsoid shape open at the bottom, a truncated cone or pyramid, an inverted chamber whose transverse vertical cross section is semi-circular, or any other suitable shape, as desired.

Whatever basic shape is selected, the major portion of the bottom edges of the end walls and side walls, taken together, constitutes the lowermost part of the assistor, which is located either (1) in a substantially horizontal plane, or (2) in a substantially horizontally disposed portion of a cylindrical surface (a) that has a circular cross section, measured in a plane transverse to the involved vein segment and (b) whose central axis is parallel to, and is positioned a substantial distance below, a straight line 142 that passes through the center of the bottom boundary of each of the notches in the end walls or (3) a generally planar surface having a wavy cross section.

FIGS. 3 and 4 provide examples of the first mentioned embodiment, which is satisfactory if the body surface on which the assistor rests during use is not too curved. FIG. 5 provides an example of the second embodiment, which is well suited for resting on a body surface that is more sharply curved. FIG. 6 provides an example of a third embodiment.

In FIG. 5, venipuncture assistor 130 has bottom edges 132 and 134 on either side of notch 136 in the near wall of the device, and on either side of a similar notch in the far wall. Bottom edges 132 and 134 lie in a curved surface that approximates the curvature of the body surface at the point where the assistor is positioned. Central axis 140 of curved surface 138 is parallel to, and is positioned a substantial distance below, a straight line 142 that passes through the center of the bottom boundary of each of the notches in the end walls.

Another embodiment of the device of this invention is illustrated in FIG. 6. In this embodiment, near side wall 148 and a similar wall on the far side connect end walls 150 and 152. Notches 154 and 156 are defined by end walls 150 and 152, respectively. Bottom edge 158 of the end walls and side walls is, except for the areas occupied by notches 154 and 156, vertically slightly wavy in form. This construction will in some cases provide a more secure positioning of the venipuncture assistor on the patient's body surface, while at the same time avoiding any sharp protuberances that would dig into the flesh surrounding the vein to be punctured.

Holding Assistor in Place

In using the embodiment of the venipuncture assistor of this invention shown in FIG. 4, the operator presses down on top wall 125 with one finger and inserts the needle somewhere in the vicinity of the location marked with the letter "X" with the other hand. The structure comprising the assistor there illustrated has a shape, especially when dimensioned as shown in FIG. 3, that can be conveniently pressed downward against the body surface by one or more of the five fingers on one of the hands of the person performing the venipuncture.

If the rest of the body part represented by top surface 116 in FIG. 4 is visualized below assistor 110, it will be seen that another of the five fingers of the same hand can be extended to contact the surface on the side of that body part. Or, in the case of a smaller body part such as a forearm, a wrist or an ankle, the second finger or thumb of the same hand can be extended to contact the opposite surface, at the bottom of the body part. In either case, the second finger or thumb can be braced against the surface in question to help stabilize the assistor and to help the operator maintain his or her balance with respect to the patient.

If the assistor takes any of the shapes discussed above other than the shape illustrated in FIG. 4, such as, for example, an inverted hemisphere or a truncated cone, a depression can, if desired, be supplied at the top of the assistor to receive downward pressure from the operator's finger or thumb.

The overall width of the assistor in the direction transverse to the vein segment should be large enough that the assistor can be held steady when positioned on the surface of the body part in which the vein is located. At the same time, the distance between the midsections of the side walls of the device should be short enough that the skin surface will be kept taut on both sides of the vein in order to help hold the vein segment steady laterally.

The overall height of the venipuncture assistors illustrated in FIGS. 4–7 is approximately one-half the largest transverse dimension of the respective assistors. As will be seen, this overall height is sufficient to provide some portion of each end wall above the notch it defines. Whatever the overall shape of the assistor, it may be lower or higher than shown in the illustrated Figures, but the overall height should not be so large that it is difficult to steady the assistor with one or two fingers when it is in operative position over a vein segment that is to be punctured. A suitable height for the assistor illustrated in FIG. 4 is about 8 mm.

FIG. 7 illustrates another embodiment 160 of the venipuncture assistor of this invention. The basic construction of the assistor is the same as the embodiment of FIG. 4—an inverted right circular cylinder 162 with a flat top 164 and a notch 166 in the bottom edge of both the near end wall and far end wall of the device. Bottom edges 168 of the side and end walls lie in a substantially horizontal plane. The bottom portion 170 of each of the side walls of the assistor is attached to a strip of material 172 that extends outwardly from the device. Means 174 (shown diagrammatically in FIG. 7) of attaching the strips to the body of the assistor can be staples, studs, glue or any other suitable means. These strips are preferably strips of adhesive tape to hold the assistor in place above the vein segment in which the needle is to b inserted. Bottom portions 170 of the end walls and side walls of the inverted chamber extend from about ½ mm. to about 1½ mm. below the points of attachment of strips 172.

While this invention has been described in connection with the best mode presently contemplated by the inventor for carrying out his invention, the preferred embodiments described are for purposes of illustration only, and are not to be construed as constituting any limitation on the invention. Modifications will be obvious to those skilled in the art, and all modifications that do not depart from the spirit of the invention are intended to be included within the scope of the appended claims.

I claim:

1. A venipuncture assistor for keeping sufficiently steady a distended selected segment of a patient's vein into which a needle is to be introduced, for the purpose of withdrawing blood from or introducing fluid into said vein, which comprises:

a cylindrical body formed of a substantially rigid material and having a vertically disposed longitudinal axis, an open bottom, a cylindrical side wall having a substantially horizontal bottom edge, and a diameter that is substantially equal to the length of said selected vein segment, said bottom edge of said cylindrical side wall containing a first vein-receiving notch at one location and a second vein-receiving notch located in a diametrically opposite portion of said cylindrical side wall, each of said first and second notches having a downwardly facing upper edge and two inwardly facing side edges, the interior of said cylindrical body containing a vein-accommodating space extending between said notches, which space is substantially free of any member that can press against said distended selected vein segment and its associated skin and tissue when said assistor is in its operative position over the vein that is to be punctured, each of said notches being configured and dimensioned to receive with an operative fit one or the other of two opposite end portions of said distended selected vein segment and its associated skin and tissue, to limit sidewise movement of the one of said opposite end portions of the distended selected vein segment that, with its associated skin and tissue, is received by said notch, and to permit whatever sidewise, downward and/or upward movement of said needle is necessary as it is being inserted into said vein segment, said vein-accommodating space extending between said notches being substantially less laterally confining than either of said vein-receiving notches, and each of said notches being substantially constant in size under any pressure that is exerted, during normal use of said assistor, on said cylinder side wall that contains said notch, said bottom edge of said cylindrical side wall and said upper edges and side edges of said notches being free of any exposed sharp protuberances in positions to press, when said assistor is in its operative position over the vein that is to be punctured, against said distended selected vein segment and its associated skin and tissue or against the surface of the body part in which said needle is being inserted, said bottom edge of said cylindrical side wall constituting the lowermost part of said assistor, which lowermost part lies in a substantially horizontal plane, whereby said venipuncture assistor can be positioned to receive said two opposite end portions of said distended selected vein segment and its associated skin and tissue within the respective notches, and said assistor can be held firmly by the operator's finger or fingers against the surface of the patient's body so as to prevent said distended selected vein segment from moving out of the path of said needle as it is inserted in said vein segment at a point adjacent one of said opposite end portions of said vein segment.

2. The venipuncture assistor of claim 1 which includes a substantially flat circular top wall, to form a cylindrical body with an open bottom and a closed top.

3. The venipuncture assistor of claim 1 which is formed of a substantially transparent material.

4. The venipuncture assistor of claim 1 in which said bottom edge of said cylindrical side wall forms a smoothly curved horizontal line that is continuous except for the areas occupied by said vein-receiving notches.

5. The venipuncture assistor of claim 1 which has an overall height of no more than about 8 mm.

6. The venipuncture assistor of claim 1 in which said cylindrical body has a diameter of about 16 mm.

7. The venipuncture assistor of claim 1 in which a strip of adhesive tape is attached to diametrically opposed portions of said cylindrical side wall between said notches, about ½ mm. to about 1½ mm. above said bottom edge of said cylindrical side wall, each of said strips extending outwardly from said assistor, whereby said assistor can be held in place above said vein segment in which said needle is to be inserted.

8. The venipuncture assistor of claim 1 in which the height of one of said notches in said bottom edge of said cylindrical side wall is greater than the height of the other of said notches.

9. The venipuncture assistor of claim 1 in which said bottom edge of said cylindrical side wall is vertically slightly wavy in form.

* * * * *